United States Patent [19]

Ishida et al.

[11] 4,318,901
[45] Mar. 9, 1982

[54] HAIR COSMETIC COMPOSITION

[75] Inventors: Atsuo Ishida, Chiba; Itomi Homma, Funabashi; Shigeo Inoue, Ichikai, all of Japan

[73] Assignee: KAO Soap Co., Ltd., Tokyo, Japan

[21] Appl. No.: 75,124

[22] Filed: Sep. 13, 1979

[30] Foreign Application Priority Data

Sep. 29, 1978 [JP] Japan .................. 53-120275

[51] Int. Cl.³ .................. A61K 7/06; A61K 7/08; A61K 7/09; A61K 7/11
[52] U.S. Cl. .................. 424/70; 424/47; 424/71; 424/72; 8/405
[58] Field of Search .................. 424/71, 70, 72; 536/115, 116

[56] References Cited

U.S. PATENT DOCUMENTS

| | | | |
|---|---|---|---|
| 3,301,848 | 1/1967 | Halleck | 536/116 |
| 3,655,645 | 4/1972 | Jacques | 536/116 |
| 4,032,702 | 6/1977 | James | 536/115 |
| 4,151,274 | 4/1979 | Schlueter et al. | 424/365 |

FOREIGN PATENT DOCUMENTS

37-4448 6/1962 Japan .................. 424/361

*Primary Examiner*—Dale R. Ore
*Attorney, Agent, or Firm*—Oblon, Fisher, Spivak, McClelland & Maier

[57] ABSTRACT

A hair cosmetic composition comprising a hydroxypropyl-etherified glycolipid ester represented by the formula,

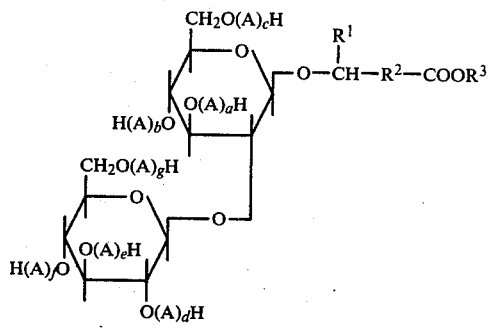

wherein $R^1$ represents a methyl group or a hydrogen atom; $R^2$ represents a saturated or unsaturated hydrocarbon group having 11 to 15 carbon atoms when $R^1$ is a methyl group, or a saturated or unsaturated hydrocarbon group having 12 to 16 carbon atoms when $R^1$ is a hydrogen atom; A represents the group

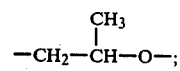

$R^3$ represents a saturated or unsaturated hydrocarbon group having 1 to 20 carbon atoms or $-(A)_hH$; and a,b,c,d,e,f,g and h are each integers and are in the range of 1 to 60 as their total number.

3 Claims, No Drawings

HAIR COSMETIC COMPOSITION

BACKGROUND OF THE INVENTION

1. Field of the Invention

This invention relates to cosmetics for use in hair treatment, more particularly to a hair cosmetic composition using a specific type of ester compound or hydroxypropyl-etherified glycolipid ester.

2. Description of the Prior Art

As is well known, hair cosmetics are generally incorporated with a plurality of ingredients called a moisturizer or an emollient in order to impart moistness and suppleness to the hair. Those ingredients which have remained deposited on the hair have hygroscopic action and serve to prevent the moisture from evaporating or escaping from inside of the hair, and therefore, are effective to keep a moisture content in the hair substantially constant and also to bring an agreeable touch to the hair. There have heretofore been used as the moisturizer polyols such as glycerine, propylene glycol and the like and peptides or amino acid derivatives such as collagen, sodium pyrrolidonecarboxylate and the like, and as the emollient hydrocarbons, higher alcohols, higher fatty acids and esters.

However, when the moisturizer mentioned above is added to a hair cosmetic such as a shampoo or rinse which requires washing after its application, it is difficult to have the moisturizer left on the hair due to its solubility in water. On the other hand, the emollient also shows a reduced tendency of remaining on the hair if used in small amounts. Use of the emollient in large amounts allows for increased deposition of the ingredient on the hair which in addition supports a good water retention ability. However, when added, for example, to a shampoo in large amounts, the emollient adversely affects the detergency of the shampoo, with the results that the shampoo not only loses its inherent properties, but also becomes oily and sticky to the touch. Consequently, the emollient is of inferior quality and performance in exhibiting an improved hair setting or redressing force or ability.

In order to impart a setting force to the hair, polypropylene glycol butyl ester and its phosphoric ester have been employed which are generally formulated in hair liquids for men. However, these compounds lack a sufficient hair setting force when used in small amounts. Large amounts increase such force to a proper degree but involve a disadvantage that the liquids feel sticky and are liable to adsorb dust and are finally hard to wash away.

Another type of ingredient useful for the purpose of setting or redressing the hair is a film-forming polymeric material such as methacryl-acrylic acid copolymer, polyvinylpyrrolidone or a vinylpyrrolidone-vinyl acetate copolymer. The polymeric material has been practically used, for example, in set lotions, hair sprays and similar cosmetics for women. When used in small amounts, such polymeric material is insufficient in the setting force, whereas large amounts are disadvantageous, though the setting force is improved, in that the polymer film becomes hard and objectionably stiff to the touch and is difficult to wash away such as with a shampoo.

In view of that situation, the present inventors have made intensive studies on a wide variety of compounds which can surmount the defects of the prior art cosmetics. As a result of these studies, they have found that a particular hydroxypropyl-etherified glycolipid ester compound meets with the desired properties and gives the best results. Based upon this finding, the present invention has been accomplished.

SUMMARY OF THE INVENTION

It is, therefore, an object of the present invention is to provide a hair cosmetic composition which can remain deposited on the hair in a high degree when added to cosmetics requiring washing after their application and which is useful for protecting the hair and imparts an agreeable finishing touch to the hair.

It is another object of the invention to provide a hair cosmetic composition which can reinforce the function of a film-forming polymeric material when added to cosmetics for hair setting or redressing and which exhibits an excellent hair setting or redressing force or ability, without giving any unpleasant sticky and stiff touch.

It is a further object of the invention to provide a hair cosmetic composition which is easy to wash away such for example as with a shampoo.

The above objects can be achieved by a hair cosmetic composition which comprises a hydroxypropyl-etherified glycolipid ester (hereinafter abbreviated as "POSL") represented by the formula (I),

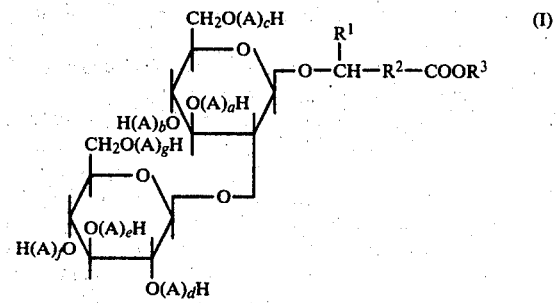

wherein $R^1$ represents a methyl group or a hydrogen atom; $R^2$ represents a saturated or unsaturated hydrocarbon group having 11 to 15 carbon atoms when $R^1$ is a methyl group, or a saturated or unsaturated hydrocarbon group having 12 to 16 carbon atoms when $R^1$ is a hydrogen atom; A represents the group

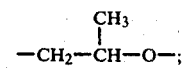

$R^3$ represents a saturated or unsaturated hydrocarbon group having 1 to 20 carbon atoms or $-(A)_hH$; and a,b,c,d,e,f,g and h are each integers and are in the range of 1-60 as their total number.

DETAILED DESCRIPTION OF THE PREFERRED EMBODIMENTS

POSL which is useful in the invention is a novel compound which can be prepared, for example, by reacting glycolipid or its ester represented by formula (II),

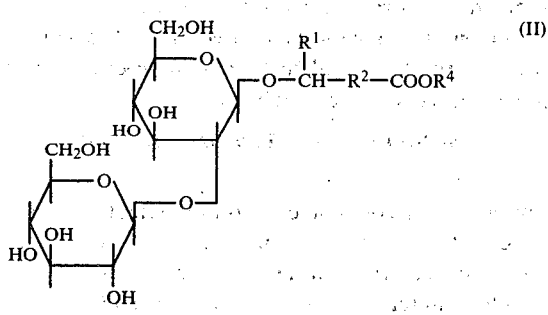

wherein $R^4$ represents a saturated or unsaturated hydrocarbon group having 1 to 20 carbon atoms or a hydrogen atom; and $R^1$ and $R^2$ are the same as defined above, with propylene oxide in the presence of an alkali catalyst (Japanese patent application No. 53-24306 now U.S. Pat. No. 4,195,177, issued Mar. 25, 1980).

The total number of carbon atoms in $R^1$ and $R^2$ of POSL should be in the range of 12-16, and the addition mole number of propylene oxide, that is, the sum of a-h, in the range of 1-60. Outside these ranges results in remarkably lowered detergency or reduced function of POSL as an oil.

POSL which is especially preferred in the practice of the invention has hydrocarbon groups wherein the total number of carbon atoms in $R^1$ and $R^2$ is in the range of 14-16, and an addition mole number of propylene oxide in the range of 5-20.

In general, POSL is an oil, sparingly soluble in water and has an oily characteristic touch. When emulsified with a surface active agent, it is readily converted into the form of an emulsion which is rather fine to the touch and can be easily washed away with water.

In practice, POSL is contained in the hair cosmetic composition in amounts of 0.1-50%, preferably 0.5-10%, based upon the weight of the composition. It is to be noted that the content may vary depending on the type of the cosmetic base ultilized. By the term cosmetic base is meant all of conventional hair cosmetics which are used to protect the hair, improve a finishing touch of the hair, set the hair right, or render handling of the hair easy and which include, for example, shampoos, rinses, treatment, hair tonics, hair liquids, pomade, set lotions, hair sprays, hair oils, cold waves, hair dyes and the like.

The hair cosmetic composition according to the invention can be readily obtained by adding POSL to these known hair cosmetics in the range of amounts defined above.

Various additives or ingredients which have been widely employed for known hair cosmetics can also be used in combination with POSL and include, for example, oils, surface active agents, alcohols, viscosity modifiers, antiseptics, drugs or chemicals, pigments, perfumes, wetting agents and water.

Suitable oils which are useful in the invention include liquid paraffin, vaseline, paraffin wax, squalane, ceresine wax, bees wax, spermaceli, carnauba wax, hardened castor oil, olive oil, tsubaki oil, lanolin, lanolin alcohol, lanolin fatty acids, higher alcohols, fatty acids, and synthetic ester oils of higher alcohols and fatty acids. Suitable surface active agents include polyoxyethylene alkyl ethers, polyoxyethylene fatty acid esters, polyoxyethylene sorbitan fatty acid esters, sorbitan fatty acid esters, glycerine fatty acid esters, polyoxyethylene glycerine fatty acid esters, polyoxyethylene hardened castor oil, polyoxyethylene sorbitol fatty acid esters, polyoxyethylene-polyoxypropylene condensate and the like. Suitable alcohols include ethanol, isopropanol and the like. Suitable viscosity modifiers include carboxylmethyl cellulose, methyl cellulose, hydroxyethyl cellulose, polyvinyl alcohol, polyvinylpyrrolidone, tragacanth gum, carrageenan, locust bean gum, dextrin, dextrin fatty acid esters, carboxyvinyl polymer, gelatin, sodium alginate, acacia and the like. Suitable wetting agents include sorbitol, glycerine, propylene glycol, 1,3-butylene glycol, sodium pyrrolidonecarbonate, lactic acid, sodium lactate, polyethylene glycol and the like. Suitable antiseptics include p-hydroxybenzoic acid alkyl esters, sodium benzoate, potassium sorbate, phenoxyethanol and the like. Further, suitable drugs or chemicals include vitamines, antiinflammatory agents and germicides.

As described above, any conventional hair cosmetic formulations can be used as the cosmetic base of the hair cosmetic composition according to the invention. These hair cosmetic formulations are well known in the art and are not discussed herein, but particular formulations of various types of hair cosmetic will be shown hereinafter for purposes of illustration only.

This invention will now be described in more detail with reference to certain specific Examples and a Reference Example for preparing POSL, which should not be construed as limiting the invention.

REFERENCE EXAMPLE (i) To a mixture of 1500 g of glucose, 75 g of a yeast extract and 15 g of urea was added water in an amount sufficient to adjust the whole amount to 15 l, and the resulting mixture was subjected to sterilization and used as a fermentation liquid. This fermentation liquid was inoculated with Torulopsis bombicola which had been cultured in a culture medium of the same composition as the fermentation liquid at 30° C. for 48 hours. The fermentation was started under the conditions: temperature of 20° C.; stirring speed of 300 rpm; and aeration rate of 0.33 VVM. The culture was conducted for 24 hours after the inoculation of the microorganisms, after which each 150 g of beef tallow was repeatedly added at intervals of 24 hours so that the total amount of beef tallow reached 900 g. After the final addition, the culture was continued for further 24 hours. The total culture time amounted to 168 hours. After the completion of the fermentation, the sophorolipid layer which had precipitated on the bottom of a fermentor was collected by decantation and filtration to obtain 1300 g of sophorolipid. The thus obtained sophorolipid was found to have a water content of about 50% and was in the form of a paste at a normal temperature.

(ii) 100 g of the thus obtained sophorolipid together with 2.5 g of polypropylene glycol having an average molecular weight of 200 was placed in a 200 ml round bottom flask equipped with a stirrer and a Liebig condenser. Thereafter, water was removed by distillation on an oil bath (80° C.) while stirring under a reduced pressure of 250 mmHg. The distillation of water was completed in about 2 hours, and the water content at that time was found to be less than 1%.

(iii) To the thus prepared sophorolipid solution in polypropylene glycol were added 150 g of methanol and then 2.5 g of sulfuric acid, followed by reaction at a temperature of 40°±2° C. for 90 minutes. The reaction was determined as having been completed by thinlayer chromatography on silica gel [developing solution: chloroform-methanol-acetic acid (75:20:5)] when a number of spots shown by the starting material or sophorolipid converged on one spot corresponding to a glycolipid methyl ester.

After the completion of the reaction, the mixture was neutralized with a predetermined amount of potassium hydroxide and then filtered. The filtrate was again placed in a round bottom flask equipped with a Liebig condenser, followed by removing methanol and methyl acetate by distillation to obtain 48 g of a brown paste mixture containing 94% of a [(2'-O-β-D-glucopyranosyl-β-D-glucopyranosyl)oxy]alkanic acid and alkenic acid methyl ester in which polypropylene glycol coexisted. This mixture was purified by column chromatography on silica gel, thereby obtaining a pure [(2'-O-β-D-glucopyranosyl-β-D-glucopyranosyl)oxy]alkanic acid and alkenic acid methyl ester.

IR (cm$^{-1}$):
  1740 ($>$C=O ester); 1380–3200 (—OH sugar); 900–750 (glucopyranose ring).

NMR [δ(pyridine)]:
  1.1–1.6 (—CH$_2$—CH$_2$—); 3.6 (—O—CH$_3$); 3.5–5.0 (sugar); 5.5 (—CH=CH— unsaturated fatty acid).

| Oil Characterization Analyses: | |
|---|---|
| Acid value: | .0 |
| Hydroxy value: | 615 |
| Saponification value: | 88 |
| Ester value: | 87 |

When 1 mole of the product was decomposed in a 5 N hydrochloric acid-methanol solution and then subjected to gas chromatography, it was found that 2 moles of methylglucoxide and 1 mole of hydroxy fatty acid methyl ester were produced.

(iv) 100 g of the thus obtained mixture of the [2'-O-β-D-glucopyranosyl-β-D-glucopyranosyl)oxy]alkanic acid and alkenic acid methyl ester and coexisting polypropylene glycol together with 0.25 g of potassium hydroxide was placed in an autoclave, into which propylene oxide gas was blown in an amount corresponding to a given addition mole number, the resulting mixture was reacted at 100° C. to 120° C. for 6 hours. After the completion of the reaction, the reaction product was neutralized with phosphoric acid, and calcium phosphate which had been formed was removed by filtration under pressure to obtain a crude product. The ethylene oxide adduct of propylene glycol was removed from the crude product by column chromatography on silica gel to obtain a pure polyoxyethylene[(2'-O-β-D-glucopyranosyl-β-D-glucropyranosyl)oxy]alkanic acid and alkenic acid methyl ester as a light yellow paste.

EXAMPLE 1

To a shampoo base of the following formulation were, respectively, added cetanol, isopropyl myristate and two kinds of POSL each in different amounts to obtain various sample shampoos. The shampoos and shampoo base were each used to wash an artificial lock of hair or toupet (80 g, 30 cm), and any varying touches of bubbles of the tested shampoos and of washed locks were compared and evaluated by a panel of ten experts. Further, each washed lock was dried under the conditions indicated below and brushed, after which the combing strength imposed on the hair was measured using a tension tester. The test results are shown in Table 1.

| Shampoo Base Formulation | |
|---|---|
| Sodium laurylpolyoxyethylene sulfate ($\bar{p}$ = 2) | 15.0% |
| Lauryldiethanolamine | 2.0% |
| Sodium benzoate | 0.2% |
| Distilled water | balance |
| | (% by weight) |

TABLE 1

| Additives to shampoos | | Amounts (%) | Touch of bubbles* | Touch of washed locks* (moistness) | Combing strength (g)** Wet condition | Combing strength (g)** Dry condition |
|---|---|---|---|---|---|---|
| Present compounds | POSL $R^1$ = CH$_3$ $R^2$ = C$_{15}$H$_{28}$ $R^3$ = —(A)$_h$—H | 1.0 | 4.0 | 4.2 | 654 | 429 |
| | | 3.0 | 4.7 | 4.8 | 627 | 403 |
| | POSL $R^1$ = CH$_3$ $R^2$ = C$_{11}$H$_{22}$ $R^3$ = CH$_3$ | 1.0 | 3.5 | 4.1 | 643 | 411 |
| | | 3.0 | 4.3 | 4.6 | 619 | 386 |
| Comparative compounds | Isopropyl myristate | 1.0 | 2.5 | 3.1 | 758 | 531 |
| | | 3.0 | 3.4 | 3.9 | 741 | 504 |
| | Cetanol | 1.0 | 2.4 | 3.3 | 738 | 481 |
| | | 3.0 | 3.8 | 3.8 | 709 | 466 |

*Note 1:
Evaluation standards for the touches or feelings for bubbles and washed locks
Very good (as compared with shampoo base alone) 5
Good (as compared with shampoo base alone) 4
Slightly good (as compared with shampoo base alone) 3
Equal to (as compared with shampoo base alone) 2
Poor (as compared with shampoo base alone) 1
**Note 2:
Measurement of combing strength 30 g of an artifical hair tress was applied and lathered with 1 g of each of the sample shampoos and rinsed. After being squeezed to remote water and dried with a towel, the tress was suspended from a strain gauge and combed down. The force imposed by such combing was determined as a wet combing strength. The tress was then allowed to stand overnight for drying in a chamber having an ambient temperature of 25° C. and a relative humidity of 60%. Then, the above procedure was repeated to measure the combing force which was determined as a dry combing strength.

As will be apparent from the test results, when added to a shampoo, rinse or like hair cosmetic of the type which is rinsed with water after its application, POSL exerts influence on the bubbling or lathering characteristics of the cosmetic to a degree equal to or greater than usually employed oils and imparts a bubbly but substantially creamy touch to the hair cosmetic. Further, since POSL shows a tendency of remaining deposited on the hair, it gives a moisted finishing touch and acts to lower the combing strength, thus mitigating possible hair damage while brushing and exhibiting superior hair protecting action.

EXAMPLE 2

A number of hair locks, each of which weighed 3.0 g and composed of completely straight hair (70–80μ thick and 21 cm long), were prepared and immersed in a 1:10 diluted solution (ethanol:water=1:1) of a hair set lotion base of the formulation indicated below. Each immersed lock was squeezed and wound in one direction around a glass tube with a diameter of 21 mm and a length of 60 mm, followed by drying at 105° C. for 3 hours and standing for 3 hours in a chamber having an ambient temperature of 20° C. and a relative humidity of 65%. Subsequently, the lock was removed from the glass tube and placed in an observation box kept under the same temperature and humidity conditions as the chamber to measure an elongation of the lock.

The results are shown in Table 2. The curl retention (%) was determined by taking as 100% the length of a lock suspended immediately after the introduction into the observation box and as 0% the original uncurled length (21 cm). The finishing touch was assessed in terms of a general agreement of a panel of five experts who had felt the respective locks with their hands after the measurement of the curl retention, while the ready-to-wash quality was evaluated by the same panel in a similar manner with respect to each lock which had been lightly washed twice with a shampoo and dried.

| Hair Set Lotion Base Formulation | |
|---|---|
| Polypropylene glycol butyl ether | 20% |
| Ethanol | 50% |
| Water | 30% |
| | (% by weight) |

TABLE 2

| Samples | | Curl retention (%) After 30 min. | Curl retention (%) After 120 min. | Finishing touch | Ready-to-wash quality |
|---|---|---|---|---|---|
| Present compounds | Hair set lotion + POSL(I)* (2%) | 86 | 80 | good | good |
| | Hair set lotion + POSL(II)** (5%) | 90 | 85 | good | good |
| Comparative compounds | Hair set lotion + PPG-BU*** (5%) | 79 | 69 | slightly sticky | rather poor |
| | Hair set lotion + PPG-Bu (10%) | 84 | 75 | sticky | poor |
| | Hair set lotion + etanol (5%) | 79 | 66 | stiff | poor |

TABLE 2-continued

| Samples | | Curl retention (%) After 30 min. | Curl retention (%) After 120 min. | Finishing touch | Ready-to-wash quality |
|---|---|---|---|---|---|
| Control | Hair set lotion alone | 75 | 62 | good | good |

*POSL(I): $R^1 = CH_3$, $R^2 = C_{15}H_{28}$, $R^3 = -(A)_hH$, a − h = 8
**POSL(II): $R^1$, $R^2$ and $R^3$ same as in POSL(I), a − h = 15
***PPG-Bu: polypropylene glycol butyl ether As will be apparent from the test results, the addition of POSL to hair set lotions increases the hair setting force, coupled with the good finishing touch and ready-to-wash quality, and the POSL-added hair set lotions are less disadvantageous than the hair set lotions containing known additives in large amounts.

EXAMPLE 3

The hair locks used in Example 2 were each wetted with water, wound around a similar glass tube and naturally dried. After the drying, the glass tube was removed, and various types of hair sprays were applied to the curled hair locks for 5 seconds, respectively. The sprayed locks were naturally dried and placed in an observation box having an ambient temperature of 30° C. and a high relative humidity of 90%. One hour after the application, the curl retention was measured in the same manner as in Example 2. The touch of the sprayed locks was also evaluated. The test results are shown in Table 3.

| Hair Spray Composition | |
|---|---|
| 2-Amino-2-methyl-1-propanol neutralized acidic acryl-methacryl polymer (Plassized L-53P made by Goo Chem. Co., Ltd.) | 1.5 % |
| Absolute ethanol | 38.5% |
| Trichlorofluoroethane | 24.0% |
| Dichlorofluoromethane | 36.0% |
| | (% by weight) |

TABLE 3

| | Samples | Curl retention (%) | Touch of treated hair |
|---|---|---|---|
| Present compounds | Hair spray composition + POSL**** (0.3%) | 83.7 | good |
| | Hair spray composition + POSL (1.2%) | 87.8 | good |
| Comparative compounds | Hair spray composition + Liquid lanolin (0.3%) | 75.1 | good |
| | Hair spray composition + Plassize L-53P (0.5%) | 82.1 | poor |
| | Hair spray composition + Plassize L-53P (1.0%) | 86.9 | very poor |
| Control | Hair spray composition | 68.0 | good |

****POSL: $R^1 = CH_3$, $R^2 = C_{15}H_{28}$, $R^3 = C_{12}H_{25}$, a − h = 15.

As will be apparent from the test results, POSL added to the usual hair spray composition serves to increase the hair setting force equally to the case where the film-forming polymer is used in increased amounts and does not give a disagreeable or stiff touch to the hair.

EXAMPLE 4

Shampoo

| Starting Materials | |
|---|---|
| (1) POSL ($R^1 = CH_3$, $R^2 = C_{15}H_{28}$, $R^3 = -(A)_hH$, a − h = 8) | 3.0% |
| (2) Sodium laurylpolyoxyethylene sulfate ($\overline{P} = 2$) | 15.0% |
| (3) Lauryldiethanolamine | 2.0% |
| (4) Sodium benzoate | 0.2% |
| (5) Propylene glycol | 10.0% |
| (6) Perfume | 0.2% |
| (7) Purified water | balance |
| | (% by weight) |

Preparation (1)–(6) were uniformly dissolved in (7) while agitating at a normal temperature to give a shampoo.

EXAMPLE 5

Rinse

| Starting Materials | |
|---|---|
| (1) POSL ($R^1 = CH_3$, $R^2 = C_{15}H_{28}$, $R^3 = C_{12}H_{25}$, a − g = 7) | 2.0% |
| (2) Distearyldimethylammonium chloride | 2.5% |
| (3) Alkylbenzene methylammonium chloride | 0.8% |
| (4) Isopropyl myristate | 1.0% |
| (5) Pigment | suitable amount |
| (6) Antiseptic | suitable amount |
| (7) Purified water | balance |
| (8) Perfume | 2.5% |
| | (% by weight) |

Preparation

To a solution of (5)–(7) maintained at 60° C. were added (1)–(4) of the same temperature under agitation. The mixture was allowed to stand, to which (8) was added at 40° C. to give a rinse.

EXAMPLE 6

Liquid

| Starting Materials | |
|---|---|
| (1) Polypropylene butyl ether (mw = 2300) | 20.0% |
| (2) POSL ($R^1 = CH_3$, $R^2 = C_{15}H_{28}$, $R^3 = -(A)_hH$, a − h = 10) | 2.0% |
| (3) Polyoxyethylene cetanol ether ($\overline{P} = 9$) | 1.0% |
| (4) Ethanol (95%) | 50.0% |
| (5) Perfume | 0.5% |
| (6) Pigment | suitable amount |
| (7) Purified water | balance |
| | (% by weight) |

Preparation

To (4) were added (1), (2), (3) and (5) for dissolution under agitation. (6) was dissolved in (7), to which was added the solution of (1)–(5) to give a uniform transparent hair liquid.

EXAMPLE 7

Hair Spray

| Starting Material | |
|---|---|
| (1) 2-Amino-2-methyl-1-propanol neutralized acidic acryl-methacrylic polymer | 1.5% |
| (2) POSL ($R^1 = CH_3$, $R^2 = C_{15}H_{28}$, $R^3 = -(A)_hH$, a − h = 5) | 0.3% |
| (3) Perfume | 0.1% |
| (4) Absolute ethanol | 38.1% |
| (5) Trichloromonofluoromethane | 30.0% |
| (6) Dichlorodifluoromethane | 30.0% |
| | (% by weight) |

Preparation (1)–(3) were uniformly dissolved in (4). A mixture of a solution of (5) and (6) was filled in an aerosol can in any usual manner to give a hair spray.

What is claimed is:

1. In a hair cosmetic composition selected from the group consisting of shampoo, rinse, hair tonic, pomade, setting lotions, hair spray, hair oil, cold wave and hair dye, the improvement which consists essentially in adding to such composition as a moisturizer about 0.1% by weight to about 50% by weight of a hydroxy-propyl-etherified glycolipid ester of the formula:

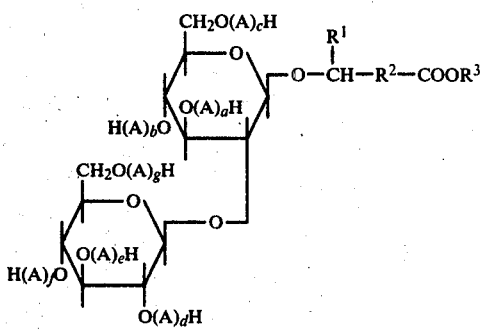

wherein $R^1$ represents methyl or hydrogen; $R^2$ represents a saturated or unsaturated hydrocarbon group having 11 to 15 carbon atoms when $R^1$ is methyl, or a saturated or unsaturated hydrocarbon group having 12 to 16 carbon atoms when $R^1$ is hydrogen; A represents the group

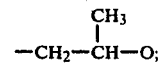

$R^3$ represents a saturated or unsaturated hydrocarbon group having 1 to 20 carbon atoms or $-(A)_hH$; and a, b, c, d, e, f, g and h are each integers and are in the range of 1 to 60 as their total number.

2. A hair cosmetic composition according to claim 1, wherein said glycolipid ester is contained in an amount of 0.5 to 10% by weight of the composition.

3. A hair cosmetic composition according to claim 1, wherein $R^1$ and $R^2$ have 14 to 16 carbon atoms in their total number, and a,b,c,d,e,f,g and h are integers of 5 to 20 in their total number.

* * * * *